United States Patent [19]
Shchervinsky et al.

[11] Patent Number: 6,126,675
[45] Date of Patent: Oct. 3, 2000

[54] BIOABSORBABLE DEVICE AND METHOD FOR SEALING VASCULAR PUNCTURES

[75] Inventors: Semyon Shchervinsky, Whitehouse Station; Louis Thomas Divilio, Neshanic; Claude Clerc, Flemington, all of N.J.

[73] Assignee: Ethicon, Inc., Somerville, N.J.

[21] Appl. No.: 09/228,211

[22] Filed: Jan. 11, 1999

[51] Int. Cl.[7] .................................................. A61B 17/08
[52] U.S. Cl. .............................................................. 606/213
[58] Field of Search ...................................... 606/213, 215; 128/898, 899; 604/32, 52, 60, 168, 285, 288

[56] References Cited

U.S. PATENT DOCUMENTS

| | | | |
|---|---|---|---|
| 5,192,302 | 3/1993 | Kensey et al. | 606/213 |
| 5,282,827 | 2/1994 | Kensey et al. | 606/215 |
| 5,383,896 | 1/1995 | Gershony et al. | 606/213 |
| 5,391,183 | 2/1995 | Janzen et al. | 606/213 |
| 5,645,566 | 7/1997 | Brenneman et al. | 606/213 |
| 5,662,681 | 9/1997 | Nash et al. | 606/213 |
| 5,690,674 | 11/1997 | Diaz | 606/213 |
| 5,810,884 | 9/1998 | Kim | 606/213 |
| 5,853,421 | 12/1998 | Leschinsky et al. | 606/213 |

FOREIGN PATENT DOCUMENTS

| | | | |
|---|---|---|---|
| WO 98/11830 | 3/1998 | WIPO | A61B 17/08 |
| WO 99/22646 | 5/1999 | WIPO . | |

*Primary Examiner*—Michael Buiz
*Assistant Examiner*—Vikki Trinh
*Attorney, Agent, or Firm*—Matthew S. Goodwin

[57] ABSTRACT

A device for sealing puncture wounds in blood vessels is open at one end and closed at the other end. The tube closure is generally flat and pivotable, and the tube region near the closed end is expandable. The device is initially contained in a sleeve, which is inserted through a cannula, so that the closed end is within the vessel to be sealed. After the cannula is removed, the closure is pivoted and the device withdrawn to a point where the closure abuts the puncture wound. After the sleeve is removed, the expandable region is expanded, so that the blood vessel wall around the puncture is sandwiched between the closure and the expanded region. The device prevents blood from seeping out of the punctured vessel during the healing process.

19 Claims, 9 Drawing Sheets

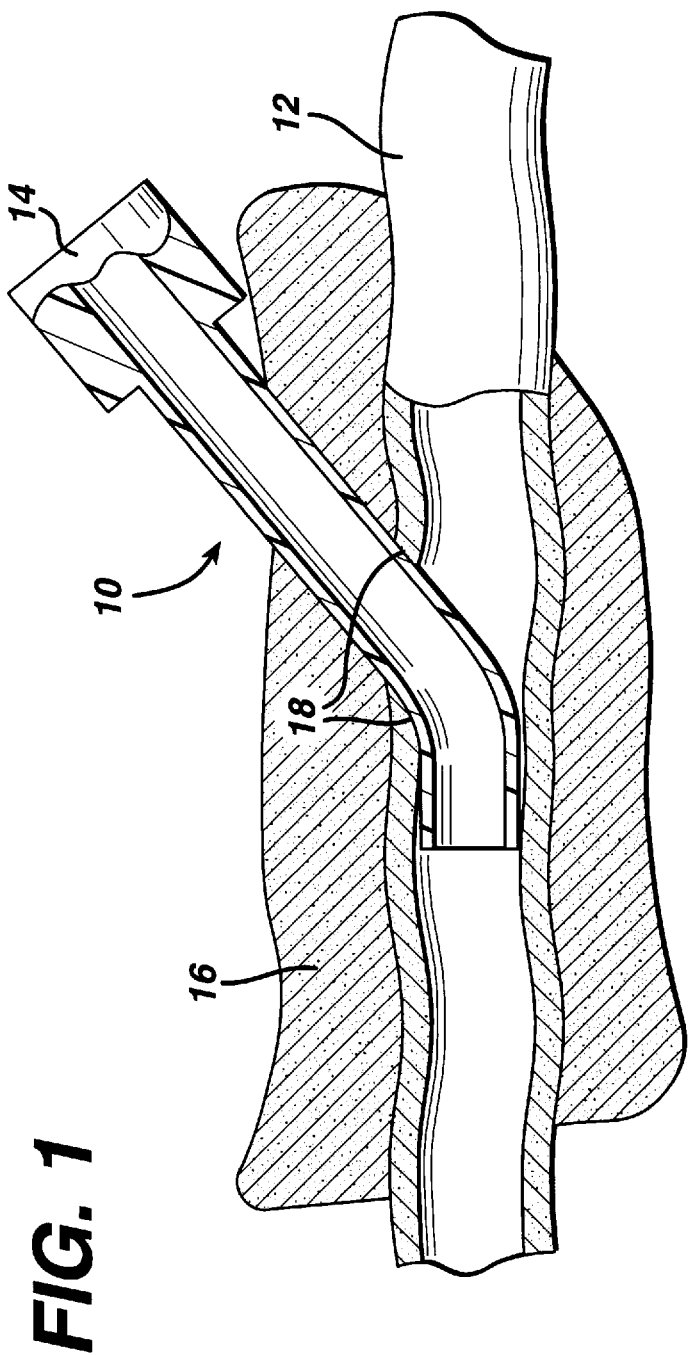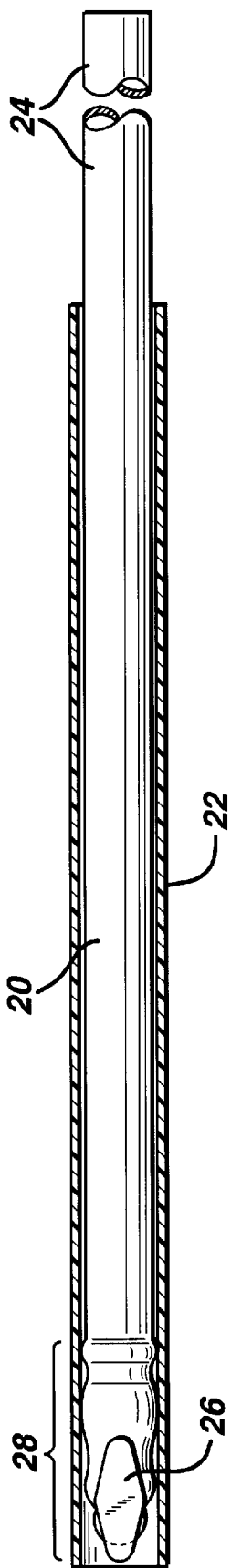

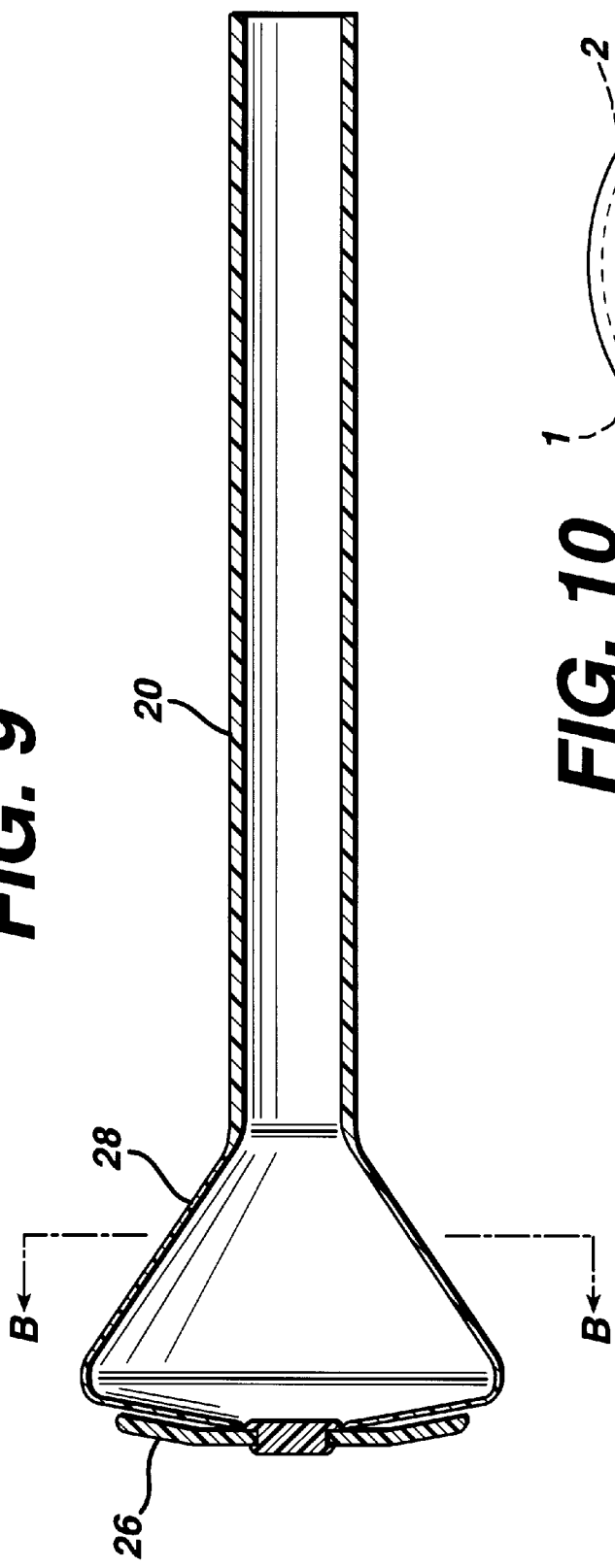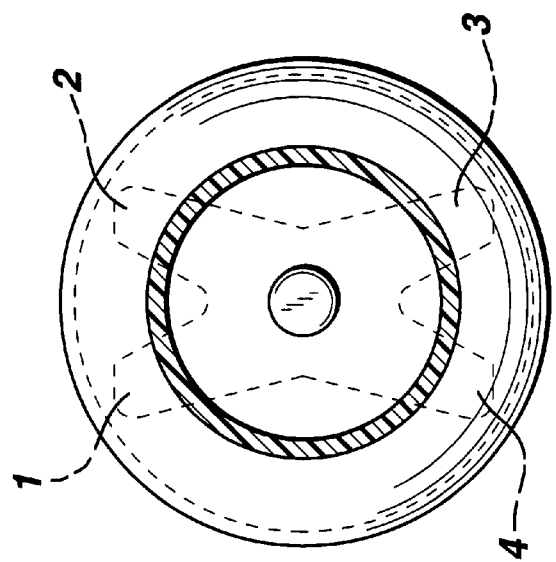

BIOABSORBABLE DEVICE AND METHOD FOR SEALING VASCULAR PUNCTURES

BACKGROUND OF THE INVENTION

1. Field of the Invention

This invention relates to a device for sealing puncture wounds in blood vessels, particularly the types of wounds that result from certain procedures in interventional medicine.

2. Description of the Related Art

A large number of medical therapeutic and diagnostic procedures involve the percutaneous introduction of instrumentation into a blood vessel. For example, percutaneous transluminal coronary angioplasty (PTCA), most often involving access to the femoral artery, is performed hundreds of thousands of times annually, and the number of other such vessel-piercing procedures performed, e.g., percutaneous coronary angiography and atherectomy, has exceeded two million per year.

In each event, the closing and subsequent healing of the resultant vascular puncture is critical to the successful completion of the procedure. Traditionally, the application of external pressure to the skin entry site by a nurse or physician has been employed to stem bleeding from the wound until clotting and tissue rebuilding have sealed the perforation. In some situations, this pressure must be maintained for half an hour to an hour or more, during which the patient is uncomfortably immobilized, often with sandbags and the like. With externally applied manual pressure, both patient comfort and practitioner efficiency are impaired. Additionally, a risk of hematoma exists, since bleeding from the vessel may continue until sufficient clotting effects hemostasis. Also, external pressure devices, such as femoral compression systems, may be unsuitable for patients with substantial amounts of subcutaneous adipose tissue, since the skin surface may be a considerable distance from the vascular puncture site, thereby rendering skin compression inaccurate and thus less effective.

Recently, devices have been proposed to promote hemostasis directly at the site of the vascular perforation. These devices can generally be grouped into two categories—"short-term" and "long-term".

Short-term devices are designed to improve on external pressure devices by applying pressure to the puncture site internally, for a limited period of time, after which the device is removed. An example of such a device is described in U.S. Pat. No. 5,383,896, issued on Jan. 24, 1995 to Gershony et al. That device consists of a shaft with an expandable balloon and guidewire tip at its distal end. A fixation collar on the shaft permits the device to be secured in place. In use, the distal end of the device is introduced into a blood vessel through an introducer sheath that is typically used in percutaneous interventional procedures. The balloon is then inflated and withdrawn until the balloon hemostatically engages the inner surface of the blood vessel, after which the introducer sheath is removed from the body. The fixation collar applies tension to the balloon for a medically sufficient period of time, after which the balloon is deflated and the entire device is removed from the body.

U.S. Pat. No. 5,645,566, issued on Jul. 8, 1997 to Brenneman et al., discloses a device that applies pressure to the outside wall of the punctured blood vessel from a distance of about 2 mm to 10 mm from the wall. It discloses various devices for applying the pressure—a balloon, a sheet supported at its corners by prongs, and a foam pad. It also describes various ways to locate accurately the pressure-applying device, such as a balloon in the vessel (similar to that of Gershony et al.) and the use of a radiopague marker.

PCT Application WO 98/11830, published on Mar. 26, 1998, S. Barak, Inventor, discloses various embodiments of an apparatus for hemostasis. Among them is a device that positions an "anchor" against an inner surface of an artery wall and a balloon outside the wall. The balloon is inflated to pinch the artery wall, after which the anchor is withdrawn. The balloon is maintained against the puncture until hemostasis is achieved.

Long-term devices are fabricated of bioabsorbable materials and are intended to remain in the body until they are absorbed. Two of these devices are available commercially, under the trademarks Angio-Seal™ (Kensey Nash Corp., Exton, Pa.) and Vasoseal™ (Datascope Corp., Montvale, N.J.).

Angio-Seal is a bioresorbable device that deploys an anchor against the inside of an artery wall and a compressed collagen sponge on the outside of the wall. The anchor and sponge are linked by a suture. (See U.S. Pat. Nos. 5,282,827 and 5,662,681).

The Vasoseal vascular hemostatic device is generally described in U.S. Pat. No. 5,391,183, issued on Feb. 21, 1995 to Janzen et al. The device inserts hemostatic material through a tissue channel and against the outside wall of the blood vessel around the puncture site.

U.S. Pat. No. 5,690,674, issued on Nov. 25, 1997 to Diaz, discloses a biodegradable plug that has two substantially parallel disks that are joined at their centers by a waist. The plug is positioned so that the distal disk is on the interior wall of the blood vessel, the proximal disk is on the exterior wall, and the waist in the wound of the vessel wall.

A description of the medical context for this invention, as well as a description of many of the prior art devices, appears in U.S. Pat. No. 5,810,884, which is hereby incorporated herein by reference. These devices typically suffer from one or more problems. They may be bulky, difficult to use, and expensive and they are not always effective at eliminating blood seepage. In some, the device may be spaced too far from the outside wall of the vessel, where there is a danger that a pseudo aneurysm may form. In others, if the device intrudes into the vessel, intravascular clots and/or collagen pieces with thrombus attached can form and embolize downstream to cause vascular occlusion. The present device addresses these problems.

SUMMARY OF THE INVENTION

The present invention provides a bioabsorbable device for sealing vascular punctures, comprising an elongated tube of substantially uniform diameter comprising a) a first end that is open, b) a second end that is closed with a substantially flat pivotable closure, having a long dimension greater than the diameter of the tube, and c) an expandable section adjoining the second end.

The closure is preferably quite small, minimally disrupting blood flow when the device is in place and thereby minimizing the likelihood of forming a thrombus. The expandable section is adapted to provide a tight seal against the blood vessel to minimize the possibility of seepage. The device is rather easy to use and is relatively inexpensive.

In use, the present invention provides a method for sealing a puncture in a wall of a blood vessel of a subject, comprising the steps of a) inserting into a cannula that has a distal end within the blood vessel and a proximal end outside the subject an elongated sleeve that contains an elongated tube comprising
  i) a proximal end that is open,
  ii) a distal end that is closed with a substantially flat pivotable closure, having a long dimension greater than the diameter of the tube, and
  iii) an expandable section adjoining the distal end;
b) conveying the distal end of the tube into the blood vessel,
c) removing the cannula from the subject, without removing the sleeve and tube,
d) conveying the tube distally, relative to the sleeve, whereby the pivotable closure extends distally from the end of the sleeve and pivots, whereby the long dimension extends substantially normal to the tube's axis,
e) conveying the tube proximally, relative to the sleeve, whereby the flat surface of the closure abuts the distal end of the sleeve,
f) conveying the tube and sleeve proximally toward the hole in the blood vessel wall until the flat surface of the closure abuts the puncture,
g) removing the sleeve from the subject, and
h) inflating the expandable section, whereby the blood vessel wall adjoining the puncture is sandwiched between the closure and the distal end of the expandable section.

BRIEF DESCRIPTION OF THE DRAWINGS

FIG. 1 is a sectional view of a cannula in a blood vessel.

FIG. 2 is a sectional view of a puncture-sealing device of this invention mounted in a sleeve.

FIG. 9 is a schematic view of the device in cross section.

FIG. 10 is a sectional view of the device of FIG. 9, taken along the axis B-B.

DETAILED DESCRIPTION OF THE INVENTION

Figure 3:
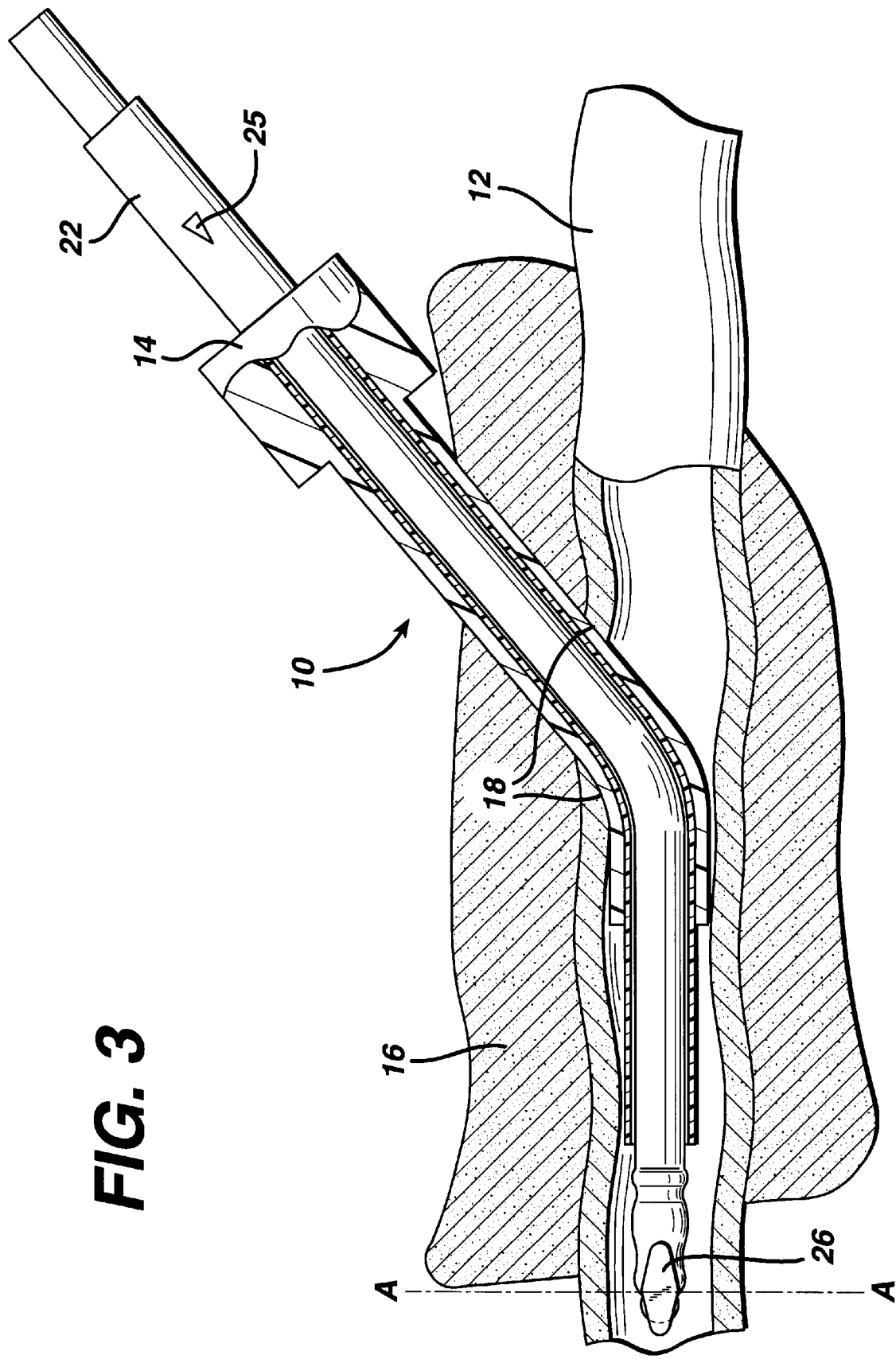
FIG. 3 is a sectional view of the device of FIG. 2 within the cannula and vessel of FIG. 1.

The present invention addresses a large and growing medical problem. As the field of interventional medicine grows, an ever-increasing number of patients must be treated for perforations in an artery or vein after percutaneous puncture of the vessel incident to an interventional catheter procedure. Two medical facts combine to exacerbate this problem. First, as compared to non-interventional catheterization, interventional catheters have significantly larger diameters, leaving larger wounds in the blood vessel wall. Secondly, interventional procedures generally require high doses of anticoagulants. The combination of these facts makes the treatment of punctured blood vessels a challenging problem for interventional medicine.

The present invention is primarily designed to seal wounds in vascular walls that result from interventional catheterization procedures for opening up blocked vessels, such as percutaneous transluminal coronary angioplasty (PTCA), atherectomy, and stent placement. One of the steps in these procedures involves inserting through the wall of a vein or artery a sheath, or cannula, over a previously introduced guidewire. The interventional catheter is introduced into the blood vessel through the cannula and is then ultimately removed.

FIG. 1 depicts the situation during an interventional procedure, after the catheter (not shown) has been removed. The distal end of cannula 10 remains within vessel 12. The proximal end 14 of the cannula is outside the body, and the intermediate region of the cannula passes through soft tissue 16 and puncture opening 18 in vessel 12.

FIG. 2 depicts a device of the present invention 20 within an introducer, or "sleeve", 22. Optionally, air in device 20 is replaced with a biocompatible or bioabsorbable filler, which must be prevented from escaping as device 20 is inserted into the body. The device has a proximal end 24 that is open and a distal end that is closed with a substantially flat pivotable closure 26, which has a long dimension aligned with the long dimension of the device when it is contained in sleeve 22. Adjoining the distal end is an expandable section 28, whose structure is generally similar to that of the balloon that is used in angioplasty. Compared with an angio balloon, the material of section 28 preferably has higher compliance and need not withstand pressures as high as those used in angioplasty.

Device 20 can be fabricated from any suitable bioabsorbable material(s). Preferred materials are polymers prepared from the following monomers: glycolide, L-lactide, D-lactide, meso-lactide, 1, 4-dioxan- 2-one, trimethylene carbonate, and e-caprolactone. These monomers can be used to prepare homopolymers, as well as copolymers, in various combinations. Preferred materials are the segmented glycolide/e-caprolactone copolymers that are used to make polyglecaprone (MONOCRYL*) sutures, the random glycolide lactide copolymers that are used to make polyglactin (VICRYL*) sutures, and the homopolymer polydioxanone, which is used to make PDS*II sutures. Information concerning these materials and processes appears in U.S. Pat. Nos. 4,490,326; 4,878,890; 5,468,253; and 5,713,920. Closure 26 can be attached to the rest of device 20 by any suitable means, such as sutures, thermal bonding, ultrasonic welding, etc. Preferably, all of device 20 is fabricated in a single piece, for example by injection molding. Since closure 26 is preferably stiffer than the remainder of device 20, it could have a greater thickness and/or reinforcing ribs.

In a particularly preferred embodiment, device 20, or part of the device, has a bioabsorbable mesh structure, either within or, more preferably, surrounding its wall and closure 26. The mesh is of a material that is absorbed more slowly than the device. Over time, tissue infiltrates the mesh and, as the wall and closure are absorbed, additional tissue infiltration provides endogenous structural support before the mesh is absorbed. Suitable materials include polyglecaprone and polyglactin for the device and mesh, respectively.

FIG. 3 shows the device of FIG. 2 after its distal end, has been inserted through the cannula of FIG. 1 into vessel 12. Once the flat closure 26 at the distal end of device 20 extends beyond the distal end of sleeve 22, it is free to pivot about axis A-A. Cannula 10 is removed from the body through soft tissue 16 and the skin, and device 20 is moved proximally, relative to sleeve 22 to reach the position shown in FIG. 4. By pulling on device 20, while holding sleeve 22 stationary, the user can ensure that a substantially flat surface of closure 26 abuts the distal end of sleeve 22. In order to assist in positioning device 20, closure 26, or another part of device 20, incorporates a radiopaque material, visible under fluoroscopy. The material is preferably a radiopaque powder, such as gold, tantalum, or barium sulfate. Although these materials are not bioabsorbable, they are endothelialized as the device is absorbed. To further assist in the proper positioning of closure 26,optional index mark 25 on sleeve 22 indicates the orientation of the device inside the body.

Figure 5:
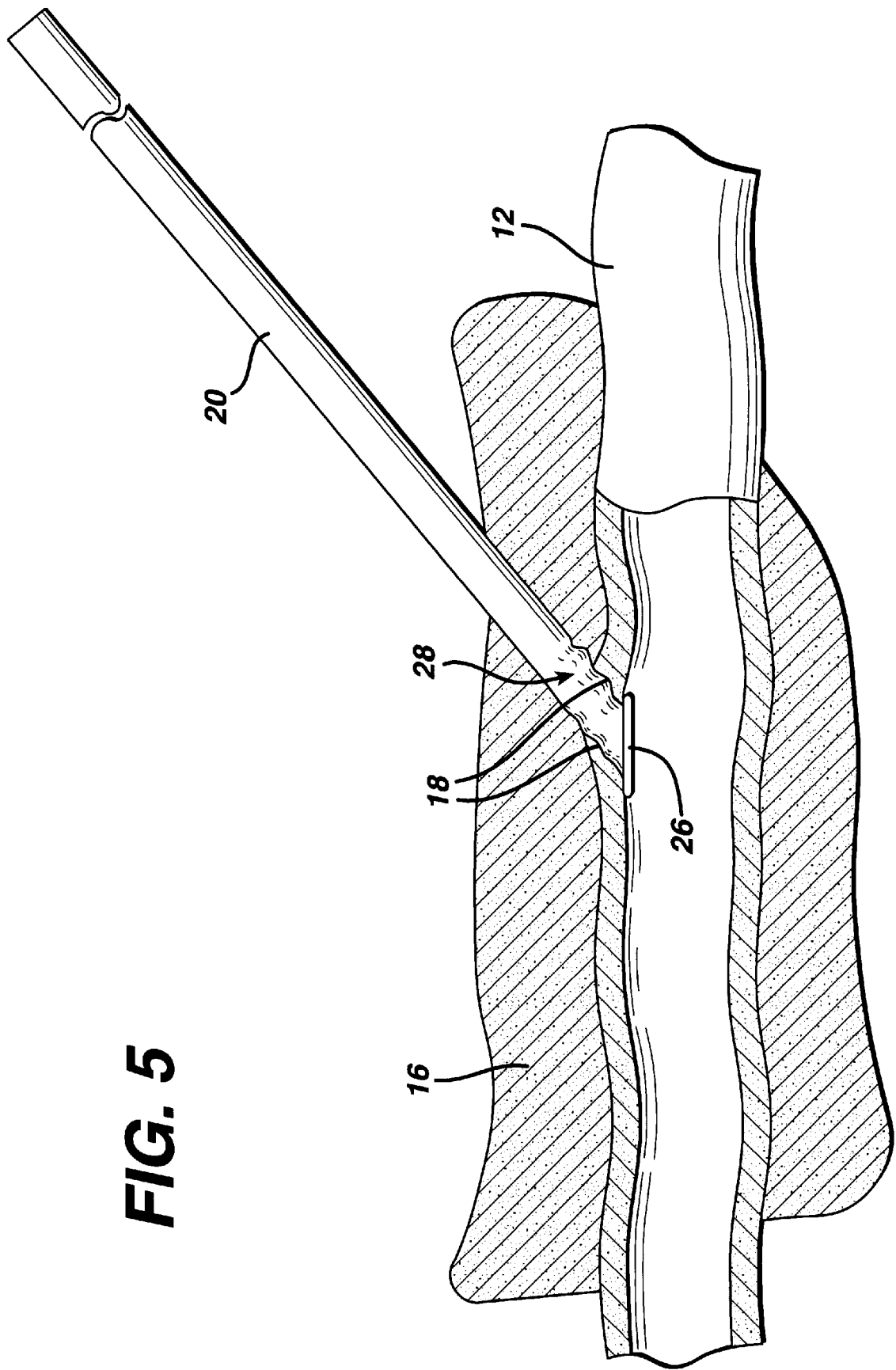
FIG. 5 is a sectional view of the device in place after the sleeve has been removed.

FIG. 5 depicts the configuration after sleeve 22 is removed from the body and device 20 is pulled in a proximal direction until closure 26 can be felt to abut puncture opening 18. At that point, expandable section 28 is bounded by the wall of opening 18 and by the soft tissue that lies outside vessel 12.

Figure 6:
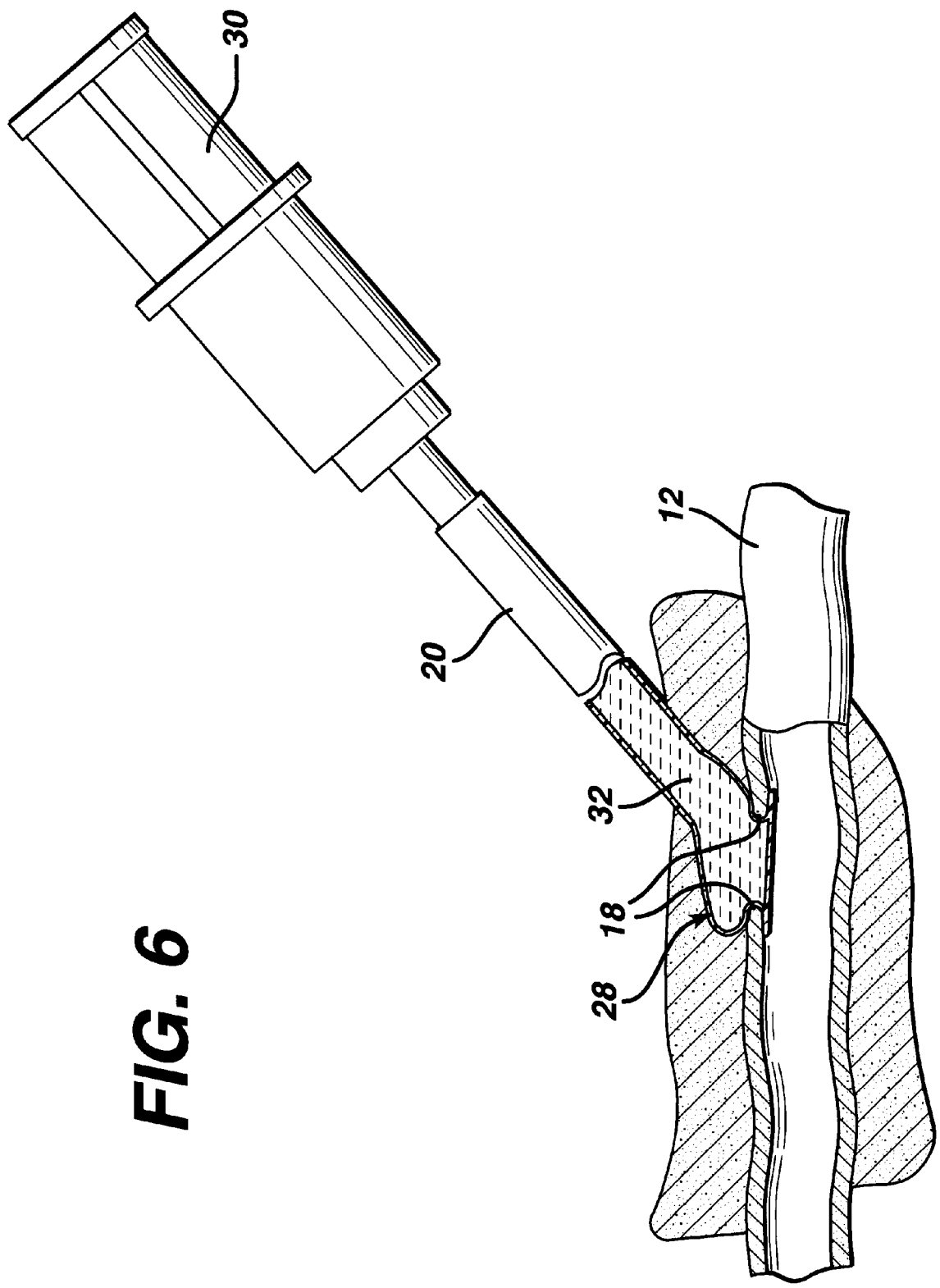
FIG. 6 is a sectional view of the device, with a syringe attached at its proximal end.

FIG. 6 shows syringe 30 attached to the proximal end of device 20. Syringe 30 contains a filler 32, which is force, into device 20 and causes expandable section 28 to expand, as shown. Alternatively, the expandable section can be prefilled with a biocompatible filler (before insertion into the body). Depending on the state of the prefill and the diameter of the tube, the proximal end of the tube may need to be sealed. Optionally, the tube may be prefilled with a material that combines with a second material introduced through syringe 30 to form a product whose volume exceeds the combined volume of the two materials, so that the product expands when the materials combine. In any case, when the tube is filled, the expandable section pushes against, and forms a fluid-tight seal with, the wall of opening 18 and the outer wall of the vessel in the vicinity of opening 18. Any suitable material can be used to expand expandable section 28—gas, liquid or flowable solid. If a gas is used, it is important to guard against the risk of embolization if the gas escapes into the vessel. A material that is solid at normal body temperature can be heated above its melting temperature and be used for filler 32. A material such as collagen, is preferred. Optionally, expandable section 28 has a coating of a surgical adhesive (such as fibrin glue) on its outer surface to enhance sealing to the surrounding soft tissue.

Figure 7:
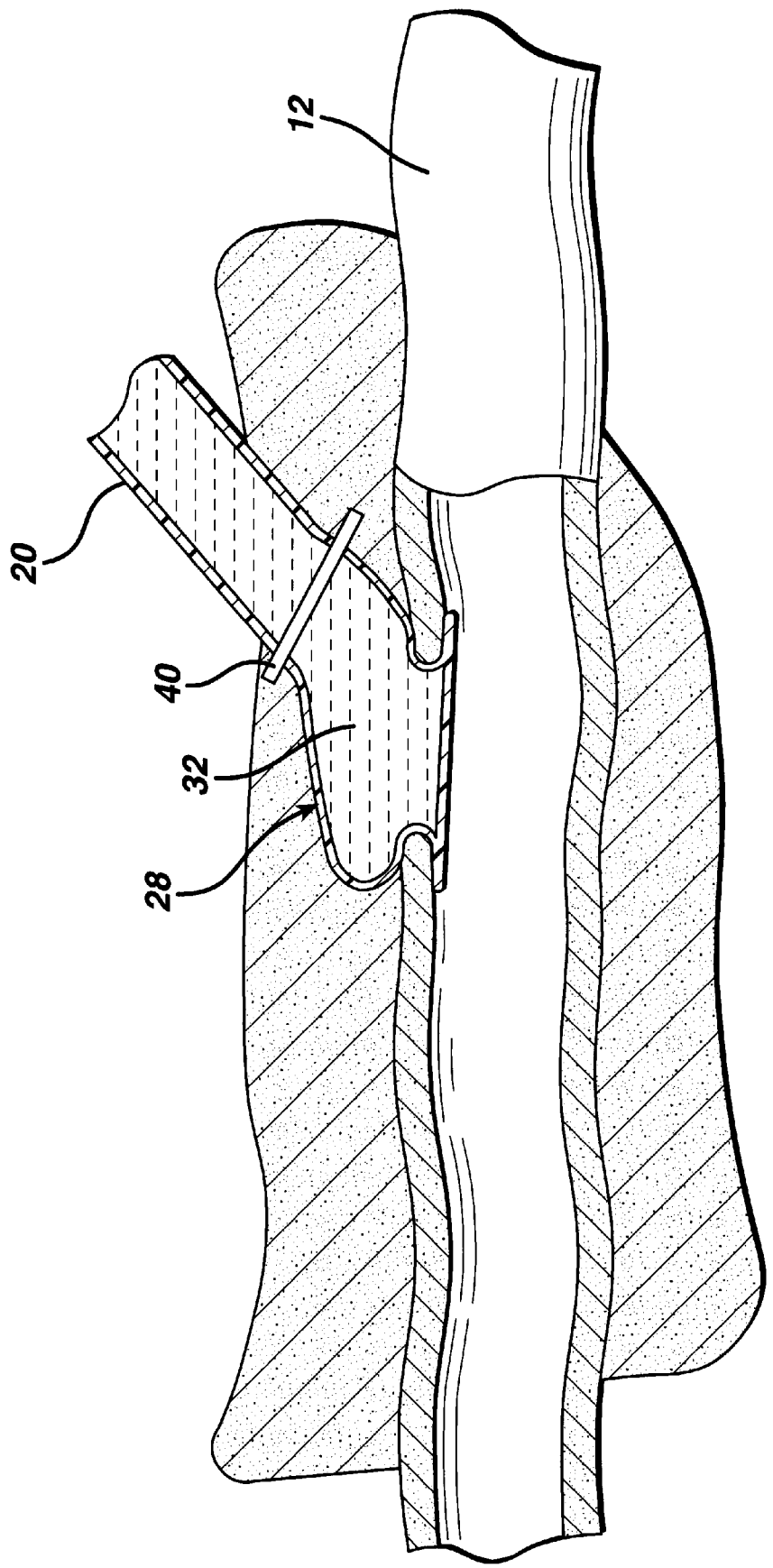
FIG. 7 is a sectional view of the device expanded and clipped off.

Once expandable section 28 has been fully expanded, if the filler 32 is not solid, ligating clamp 40 is applied to device 20, as shown in FIG. 7, to keep expandable section 23 inflated and thereby maintain the pressure on the wound site and adjoining vessel wall. Preferably, filler 32 and clamp 40 are bioabsorbable, and device 20 is cut between the proximal end of clamp 40 and the skin line. Long term, all of device 20, including filler 32 and clamp 40, are absorber by the body. The pressure applied by expandable section 28 to the area at and around the wound site ensures that the wound in the vessel wall will be healed before the device is absorbed. Alternatively, if filler 32 is not bioabsobable, then it can be removed, if necessary, once expandable section 28 is secured to the surrounding soft tissue.

Figure 8:
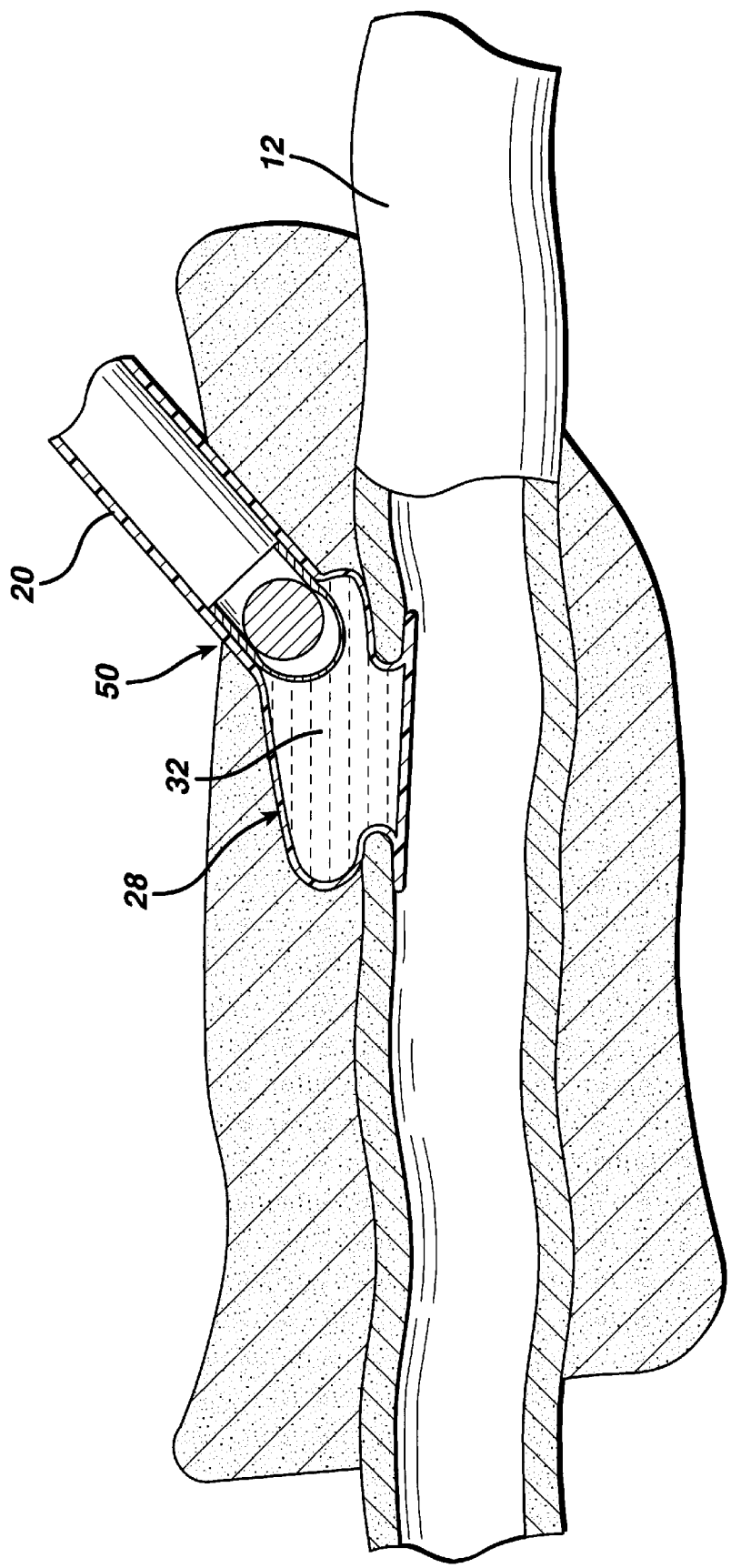
FIG. 8 is a sectional view of an alternative embodiment of the device.

FIG. 8 depicts an embodiment that uses a check valve 50 in place of clamp 40 to ensure that filler 32 does not flow out of expandable section 28.

FIG. 9 is an idealized sectional view that shows that expandable section 28, when expanded, preferably forms a cone, whose base closely adjoins closure 26 and whose top opens into the proximal section of device 20. The region between closure 26 and expandable section 28 is constricted to a smaller diameter than the proximal region of device 20.

Also apparent in FIG. 9 is the preferred shape of closure 26—concave facing the remainder of device 20.

Figure 4:
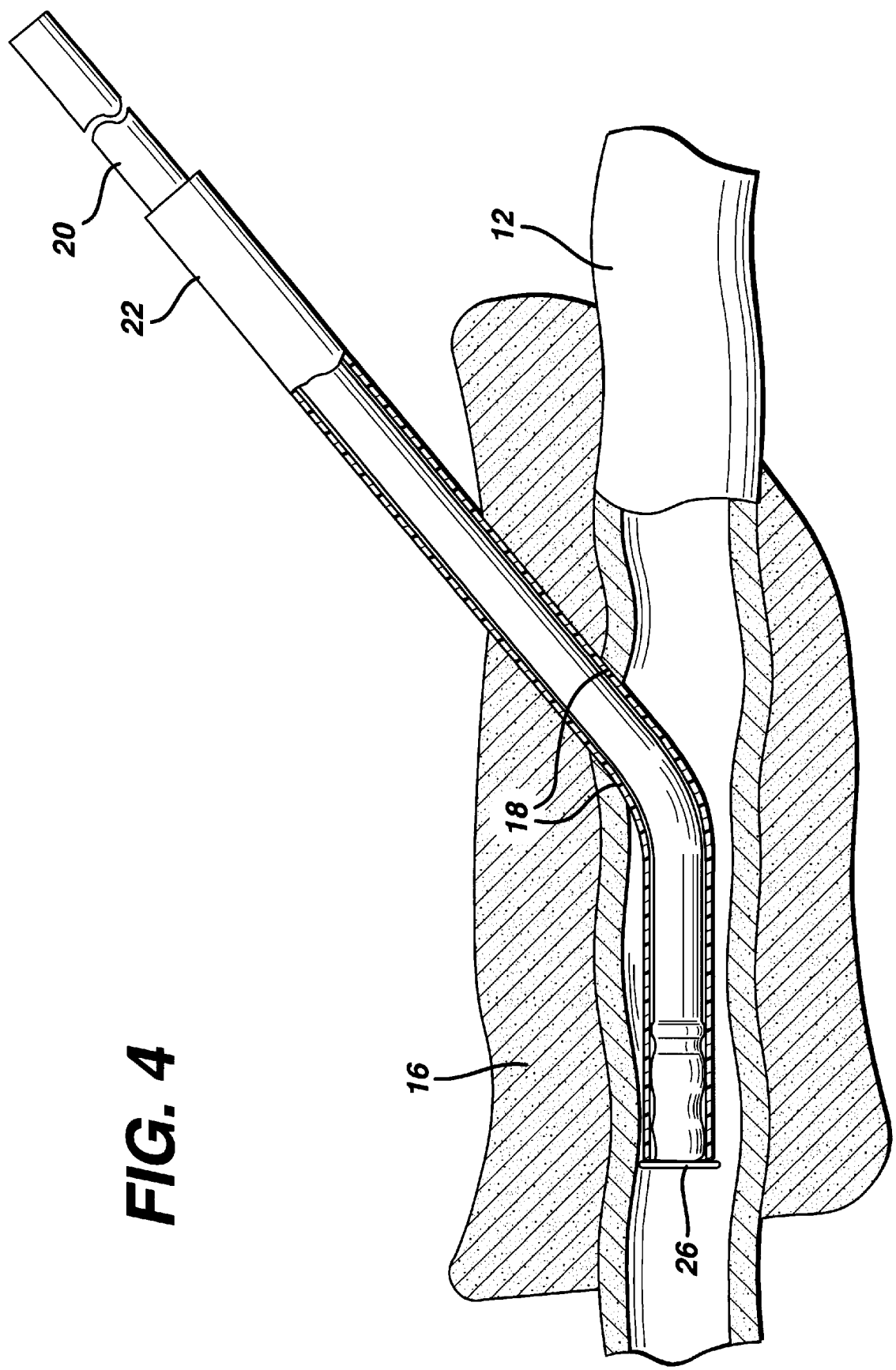
FIG. 4 is a sectional view of a later stage of device placement, after the cannula has been removed.

FIG. 10 depicts an optional X-shaped closure, whose 4 legs—1, 2, 3, and 4—each pivot into their extended configuration only after sleeve 22 is removed (as shown in FIGS. 3 and 4).

Figure 11:
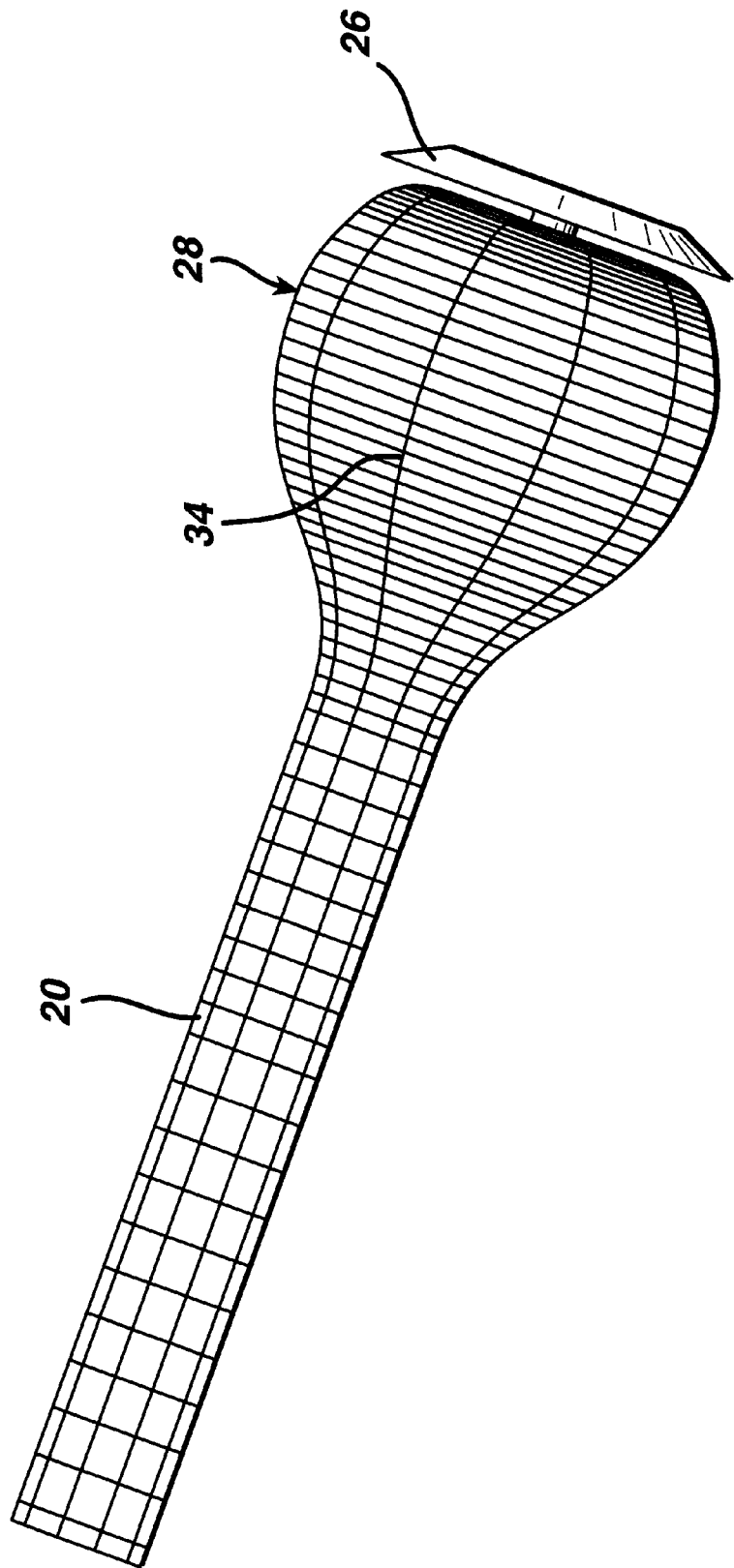
FIG. 11 is a perspective view of yet another embodiment of the device.

FIG. 11 depicts an embodiment of the device in which optional mesh 34 surrounds the wall and closure of device 20.

It will be understood by those skilled in the art that the foregoing description and Figures are illustrative of practicing the present invention, but are in no way limiting. Variations of the detail presented herein may be made without departing from the scope and spirit of the present invention.

We claim:

1. A bioabsorbable device for sealing vascular punctures, comprising:
   i) an elongated tube of substantially uniform diameter comprising
      a) a first end that is open
      b) a second end that is closed with a substantially flat pivotable closure, having an axial dimension greater than the diameter of the tube, and
      c) an expandable section adjoining the second end; and
   ii) a bioadsorbable mesh surrounding the tube.

2. The device of claim 1, wherein the device is one piece.

3. The device of claim 1, wherein the device incorporates a composition selected from the group consisting of polyglecaprone, polyglactin, and polydioxanone.

4. The device of claim 1, wherein the device incorporates a radiopaque material.

5. The device of claim 1, in which air in the device has been replaced with a biocompatible filler.

6. The device of claim 1, wherein the device has a closure at the second end of the elongated tube, and the closure is concave and facing the open first end.

7. The device of claim 1, in which the closure has a dimension less than the diameter of the tube.

8. The device of claim 1, in which the closure is substantially X-shaped.

9. The device of claim 1, further comprising a constricted region of reduced diameter between the expandable section and the second end.

10. The device of claim 1, in which the expandable section contains a first material that can combine with a second material to form a product whose volume is greater than the combined volumes of the first and second materials.

11. The device of claim 1 further comprising a coating of tissue adhesive on at least a part of the outside of the expandable section.

12. The device of claim 1, in which the expandable section, when expanded, substantially has the form of a truncated cone, whose base adjoins the second end.

13. The device of claim 1, in which the tube further contains a check valve between the expandable section and the first end, whereby fluid may pass through the valve into, but not out of, the expandable section.

14. The device of claim 6, wherein the bioabsorbable mesh surrounds the closure, and the tube and closure are more rapidly bioabosorbable than the surrounding mesh.

15. The device of claim 1, further comprising an elongated sleeve for surrounding the device.

16. The device of claim 15, in which the sleeve has an index mark on or near one end to provide orientation information.

17. A method for sealing a puncture in a wall of a blood vessel of a subject, comprising the steps of
   a) inserting into a cannula that has a distal end within the blood vessel and a proximal end outside the subject an elongated sleeve that contains an elongated tube comprising
      i) a proximal end that is open,
      ii) a distal end that is closed with a substantially flat pivotable closure, having an axial dimension greater than the diameter of the tube, and
      iii) an expandable section adjoining the distal end;
   b) conveying the distal end of the tube into the blood vessel,
   c) removing the cannula from the subject, without removing the sleeve and tube,
   d) conveying the tube distally, relative to the sleeve, whereby the pivotable closure extends distally from the end of the sleeve and pivots, whereby the long dimension extends substantially normal to the tube's axis,
   e) conveying the tube proximally, relative to the sleeve, whereby the flat surface of the closure abuts the distal end of the sleeve,
   f) conveying the tube and sleeve proximally toward the hole in the blood vessel wall until the flat surface of the closure abuts the puncture,
   g) removing the sleeve from the subject, and
   h) inflating the expandable section, whereby the blood vessel will adjoining the puncture is sandwiched between the closure and the distal end of the expandable section.

18. The method of claim 17 in which the expandable section is inflated with a bioabsorbable material.

19. The method of claim 17 in which the expandable section is inflated with a gas.

* * * * *